(12) United States Patent
Fischer

(10) Patent No.: US 10,010,672 B2
(45) Date of Patent: Jul. 3, 2018

(54) ACTIVE EMERGENCY SUPPLY VALVE

(71) Applicant: SciPharm SàRL, Luxembourg (LU)

(72) Inventor: Georg Fischer, Stanz (AT)

(73) Assignee: SciPharm SàRL, Luxembourg (LU)

( * ) Notice: Subject to any disclaimer, the term of this patent is extended or adjusted under 35 U.S.C. 154(b) by 0 days.

(21) Appl. No.: 14/890,862

(22) PCT Filed: May 16, 2014

(86) PCT No.: PCT/EP2014/060117
§ 371 (c)(1),
(2) Date: Nov. 12, 2015

(87) PCT Pub. No.: WO2014/184358
PCT Pub. Date: Nov. 20, 2014

(65) Prior Publication Data
US 2016/0129179 A1 May 12, 2016

(30) Foreign Application Priority Data
May 16, 2013 (EP) ..................... 13168018

(51) Int. Cl.
A61M 5/145 (2006.01)
A61M 5/168 (2006.01)
(Continued)

(52) U.S. Cl.
CPC .... *A61M 5/14526* (2013.01); *A61M 5/14276* (2013.01); *A61M 5/16831* (2013.01);
(Continued)

(58) Field of Classification Search
CPC ............ A61M 5/14276; A61M 5/1452; A61M 5/14526; A61M 5/16831; A61M 5/16854;
(Continued)

(56) References Cited

U.S. PATENT DOCUMENTS 4,886,499 A * 12/1989 Cirelli ................... A61M 5/142
128/DIG. 12
6,102,887 A * 8/2000 Altman ............. A61M 25/0084
604/22

(Continued)

FOREIGN PATENT DOCUMENTS

| WO | 2007/051563 A1 | 5/2007 |
| WO | 2008/106810 A1 | 9/2008 |
| WO | 2010/040556 A2 | 4/2010 |

OTHER PUBLICATIONS

International Search Report and Written Opinion for PCT/EP14/60117 dated Nov. 10, 2014; 21 pages.
(Continued)

*Primary Examiner* — Laura Bouchelle
*Assistant Examiner* — Tasnim M Ahmed
(74) *Attorney, Agent, or Firm* — Loza & Loza, LLP; Michael Fedrick

(57) ABSTRACT

The present invention provides an emergency supply valve to support the in situ administration of a drug to a subject in need thereof, comprising an infusion needle connected to a movable piston, wherein said piston is forwarded by infusion solution unable to pass the regular drug line due to kinking or obstruction thereof, a self-sealing membrane that is disrupted by the infusion needle when the piston is in a forward position, a connecting unit that connects the needle to the regular drug conduit when the needle is in a forward position, and a pressure sensitive mechanism that retracts the piston from the forward position when an increased pressure of the drug supply is normalized and its use for the treatment of subjects in need thereof.

18 Claims, 3 Drawing Sheets

Figure 1:
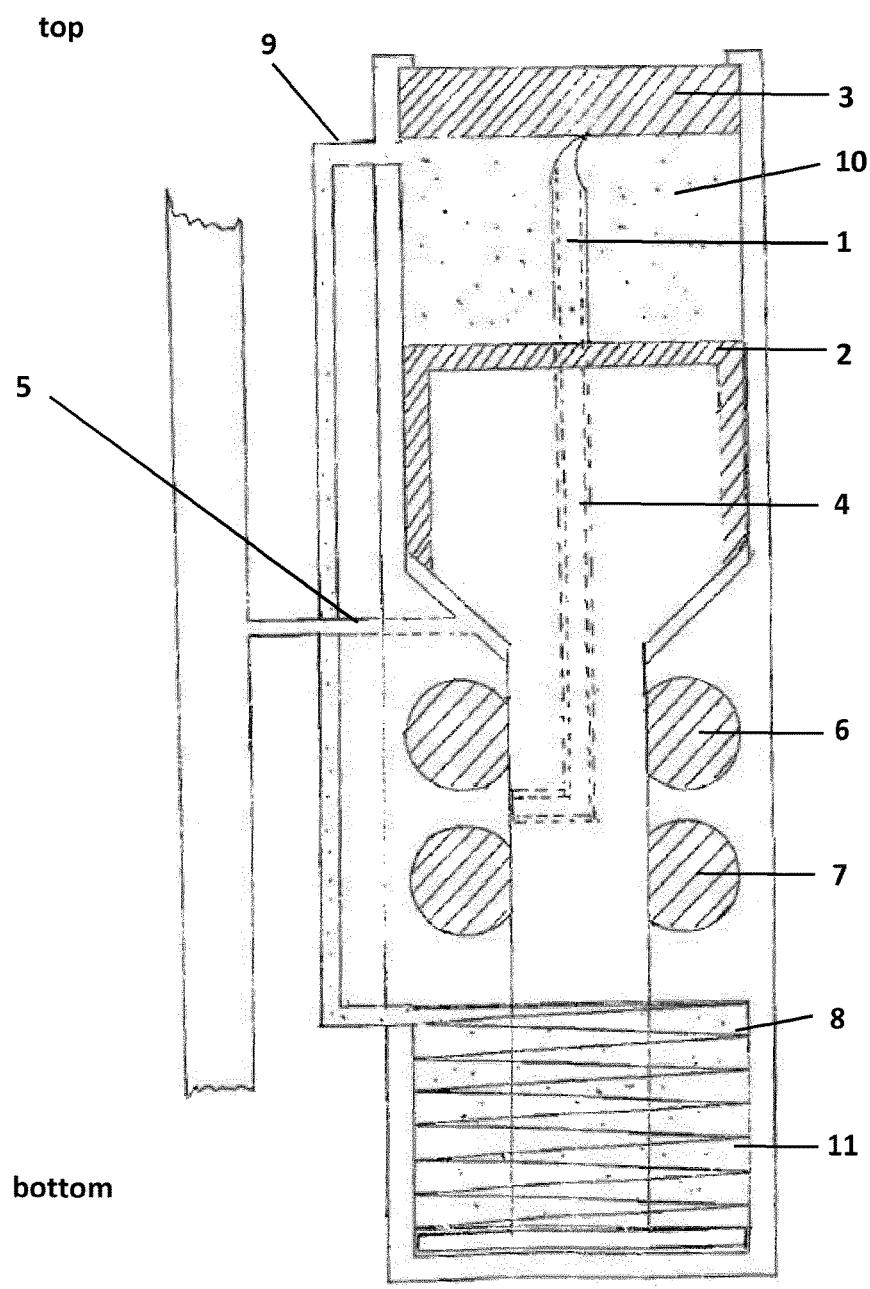

(51) Int. Cl.
  *A61M 5/142* (2006.01)
  *A61M 39/22* (2006.01)
  *A61M 39/24* (2006.01)

(52) U.S. Cl.
  CPC ..... *A61M 5/16854* (2013.01); *A61M 5/16877* (2013.01); *A61M 39/221* (2013.01); *A61M 39/24* (2013.01); *A61M 2005/14284* (2013.01); *A61M 2005/16863* (2013.01); *A61M 2205/16* (2013.01); *A61M 2205/18* (2013.01); *A61M 2205/32* (2013.01); *A61M 2205/581* (2013.01); *A61M 2205/582* (2013.01)

(58) Field of Classification Search
  CPC .. A61M 39/227; A61M 39/24; A61M 39/221; A61M 2005/14533; A61M 2005/14284; A61M 2005/16863; A61M 2205/16; A61M 2205/18; A61M 2205/582
  See application file for complete search history.

(56) References Cited

U.S. PATENT DOCUMENTS

| | | |
|---|---|---|
| 2003/0216683 A1 | 11/2003 | Shekalim |
| 2009/0076485 A1 | 3/2009 | Mubarak |
| 2012/0078181 A1 | 3/2012 | Smith et al. |
| 2012/0234433 A1 | 9/2012 | Shih et al. |

OTHER PUBLICATIONS

Extended European Search Report for 13168018.3 dated Feb. 3, 2014; 11 pages.

\* cited by examiner

ACTIVE EMERGENCY SUPPLY VALVE

CROSS-REFERENCE TO REALTED APPLICATIONS

This application is the U.S. national stage of International Patent Application No. PCT/EP2014/060117, filed on May 16, 2104 and entitled NOVEL ACTIVE EMERGENCY SUPPLY VALVE, which claims the benefit of priority under 35 U.S.C. § 119 from European Patent Application No. 13168018.3, filed May 16, 2103. The disclosures of the foregoing applications are incorporated herein by reference in their entirety.

FIELD OF THE INVENTION

The present invention provides an emergency supply valve to support the in situ administration of a drug to a subject in need thereof, comprising an infusion needle connected to a movable piston, wherein said piston is forwarded by infusion solution unable to pass the regular drug line due to kinking or obstruction thereof, a self-sealing membrane that is placed in front of the needle tip and that is disrupted by the infusion needle when the piston is in a forward position, a connecting unit that connects the needle to the regular drug conduit when the needle is in a forward position, and a pressure sensitive mechanism, specifically a retention spring, that retracts the piston from the forward position when increased overpressure of the drug supply is normalized.

BACKGROUND OF THE INVENTION

Implantable drug infusion devices are well known in the art and are considered to provide patients with prolonged dosage or infusion of a therapeutic agent. Active drug infusion devices feature a pump or metering system to deliver the drug into a patient's system and usually contain electronic pressure sensors and processors. Implantable medical devices that supply ambulatory patients with medication must have a manner of alerting patients to relevant events. Several different alert systems are already used in combination with implantable pumps or other devices, like acoustic or vibration signals.

However, specifically when the infusion device provides with a medication that is essential for the patient and wherein any interruption of said supply would lead to a life threatening event, an efficient alarm system is even more important.

As an example, pulmonary arterial hypertension is a disabling and life threatening disease which, without adequate therapy, has a very poor prognosis quoad vitam. Parenteral prostanoid analogues to date still belong to the most active compounds for the management of this disease. Such therapy must be given lifelong without any interruption. Any treatment interruption could result in hypertensive crisis in the lung circulation which might end up in fatal acute right heart failure. External high precision micropumps serve as technical administration aids which provide permanent subcutaneous or intravenous drug delivery. In order to alert patients when vital drug supply is disrupted, e.g. due to catheter kinking or occlusion, these pump devices are equipped with acoustic occlusion alarms.

External pumps are stigmatising and in the case of a central venous access linked to a substantial risk of catheter infection and sepsis. The latest micropump devices may now be implanted into the subcutaneous space of the right or left lateral lumbar region. These pumps have the advantage of providing well tolerated intravenous drug administration without the risk of infections inherent to external catheters. Monthly refill intervals ensure further patient compliance and convenience. Acoustic alarm systems built into implantable micropumps face numerous technical disadvantages. Acoustic signals which are released underneath the skin are rather silent and may be missed especially during night time. Moreover, acoustic signal sources require a battery which may wear out rapidly, if the occlusion could not be removed within a short time. Batteries would also wear off, if repeated alarm situations did occur. Thus an implanted pump device which per se should last for close to 10 years might have to be replaced due to alarm battery failure after just some days.

In practice, even more important is that an alarm poses a sole awareness measure without resolving the possibly fatal consequences of the stopping of a prostanoid delivery. If such an alarm happened, e.g., when travelling abroad, then there might be no infrastructure available to solve this sudden life threatening treatment halt.

US2009/0076485A1 describes a safety system for implantable pumps with two catheters, which is unprotectedly exposed to the patient's tissue. Thus the emergency outlet of the second back up catheter may within a short period be encapsulated and occluded by a connective tissue capsule which is built by the body's system and thereby rendered ineffective.

US2003/216683A1 describes a delivery device for metered drug delivery comprising an electronic pressure measurement system and a controller that selectively opens the valves to steadily release a defined quantity of a liquid medicament.

WO2008/106810A1 discloses a hydraulic occlusion detection system integrated in a medical device.

US2012/0078181A1 describes infusion pumps with a cartridge body with a reservoir and an outlet port and a manifold connected to said body, having a through-bore in fluid communications with said outlet port.

Thus, there is still an unmet need to provide an emergency system that makes sure that the patient gets aware of said malfunction as soon as possible and wherein constant supply of the medication is still provided even when the regular supply systems are disturbed.

SHORT DESCRIPTION OF THE INVENTION

The object is achieved by the present invention which provides a novel emergency system that constantly provides a subject with the respective medication, avoids any interruption in the drug supply and additionally alerts the subject with an alarm characterized by local irritation or pain at the back-up drug infusion site. Additionally, the present invention provides an emergency system that is fully functional without the need of an energy source like batteries. Even if the drug would not cause any irritation, the inventive system would still be useful for continuous drug supply if the intravenous delivery occluded. Upon routine X-ray surveillance it may then be detected whether the drug is supplied via the regular intravenous system or via the alternative route due to the system of the invention.

The present invention provides an active emergency supply valve which warrants continuous drug delivery by rerouting the infusion in case of blocked venous line into the subcutaneous tissue. This is securely accomplished by a pressure activated injection mechanism which is able to overcome connective tissue barriers. Such tissue barriers do encapsulate all implants after prolonged periods and would per se gradually obstruct unprotected static outlets for alternative drug delivery.

The active emergency supply valve renders electronic alarm systems redundant and may safeguard permanent drug delivery by means of an uncomplicated robust mechanical solution. However, the setup containing the emergency supply valve of the invention may further contain additional acoustic or vibration alarm systems.

According to the embodiment of the present invention an emergency supply valve to support the in situ administration of a drug solution to a subject in need thereof is provided, based on the concept of a dual outlet administration device, which in case of failure of the regular delivery route activates the second delivery route by means of a device.

Specifically, the invention provides a device supporting the administration of a drug fluid comprising
  a. an infusion needle connected to a movable piston,
  b. a pressure sensitive system that allows the piston to move into a forward position at an increased overpressure of the drug solution that is unable to pass the regular drug supply line,
  c. a self-sealing membrane placed in front of the needle tip,
  d. a connecting unit attached to the needle, wherein the connecting unit is sealed off the regular drug conduit when the needle is in the retracted state and is connected to the regular drug conduit when the needle is in the forward state and is penetrating the membrane.

According to an embodiment of the invention, the valve is further comprising a supporting line connecting the regular drug supply conduit with a) the pressure sensitive system, b) the chamber containing the needle and/or c) the connecting unit.

According to a further embodiment of the invention, the valve is comprising a supporting line connecting the pressure sensitive system and the chamber containing the needle.

In a further embodiment, the piston comprises surfaces upon which the pressure of the fluid in the regular drug supply line acts.

According to a further embodiment of the invention, the pressure sensitive system may specifically comprise a retaining spring that retracts the piston from the forward position. Specifically, said retaining spring is directly connected to or combined with the movable piston.

Specifically, the piston overcomes the resistance of the pressure sensitive system in the presence of an increased drug overpressure.

Pressure of drug supply may be higher than the body pressure to provide continuous flow of the drug solution and can be defined as normal overpressure $P_1$,—Increased overpressure is defined as $P_2$, with the proviso that $P_2>P_1$.

According to a further embodiment, the drug is normally administered intravenously to provide sufficient drug supply, whereas in the emergency supply the drug fluid is administered subcutaneously.

According to an embodiment, the needle is a hollow needle with a beveled tip.

The optimum length of the infusion needle can be easily determined by the skilled person and depends on the size of the emergency supply valve. Specifically, when moved into the forward position, the infusion needle has a length sufficient to penetrate the membrane, which is in the vicinity of the tip. More specifically, said tip is in tight contact to the membrane but not penetrating said membrane when being in the resting position and is designed to pass through the membrane and the scar tissue capsule around the outer surface of the membrane in the forward position. This may be accomplished by about 3 to 5 mm excess length.

In a further embodiment of the invention, the emergency supply valve comprises one or more sealing rings, wherein said sealing rings are placed behind the opening for the connecting unit.

According to an embodiment, the self-sealing membrane can be made from polymeric material, specifically said polymeric material may comprise at least one polymer selected from silicon and polyurethane.

According to a specific embodiment, the metal parts such as but not limited to the retaining spring and the needle are made of non-magnetizable material.

According to a further specific embodiment, increased overpressure in the drug supply line coupled to the emergency supply valve, moves the piston into forward position and thereby switches the valve into the alternative administration mode. Said increased overpressure may be due to blockage of the intravenous infusion device or outlet port.

In a specific embodiment of the invention, a supplement line is provided, connecting the drug supply conduit and the emergency supply valve, which may be part of the conduit or specifically connected and sealed thereto.

According to a further embodiment, the needle is in resting position up to an overpressure threshold of ≤200 kPA, specifically up to an overpressure threshold of ≤150 kPA, specifically up to an overpressure threshold of ≤100 kPA.

According to a further embodiment, the needle is forwarded with increasing overpressure of >200 kPA, specifically with increasing overpressure of >150 kPA, specifically with increasing overpressure of >100 kPA, wherein the increasing pressure does not exceed 250 kPA.

According to a further embodiment, the connecting unit gains access to the regular infusion conduit once the needle has been pushed past the septum or membrane into the subcutaneous tissue, specifically when the infusion needle is in the forward position. The present invention also provides a setup or device comprising an implantable pressure pump and a supply unit, wherein the supply unit comprises
a) an output line
b) the emergency supply valve according to the embodiment of the invention connected to the output line or to a supporting line, wherein
the output line constantly supplies the drug intravenously to a subject and
the emergency supply valve administers said drug by an alternative administration mode and
wherein said valve is placed between the pump and a central venous access point.

According to an embodiment of the present invention, the emergency supply valve of the invention or the setup containing the emergency supply valve is covered by a housing which allows suturing of the housing into the surrounding tissue at several points to secure its immobility at the implantation site.

According to a further embodiment, a preceding pump further may comprise a power source and a refillable drug containing reservoir, specifically the preceding pump may contain a self-sealing service port which allows rinsing of the output line and thereby resetting of the emergency supply valve.

According to a further embodiment, restoring of the regular supply pathway via the central venous catheter brings the infusion needle back to its resting position.

The present invention also provides a method for administering a drug to a subject in need thereof by using the emergency supply valve in a setup.

According to the embodiment, a drug solution is administered that causes mild to moderate local pain or irritation upon subcutaneous administration by the emergency supply valve and thereby alerts the individual to seek medical aid, specifically while maintaining continuous drug supply.

FIGURES

Figure 2:
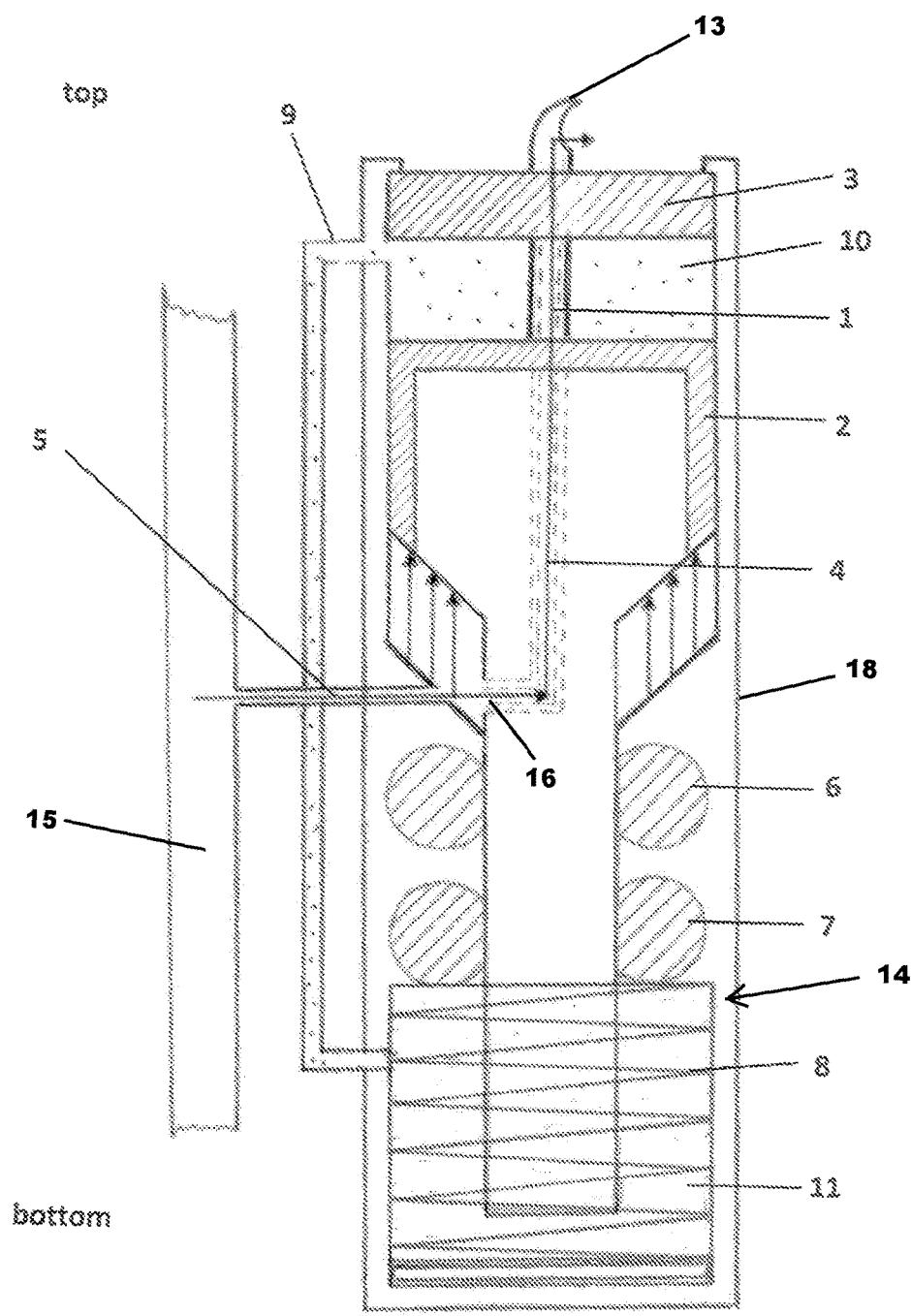
Figure 3:
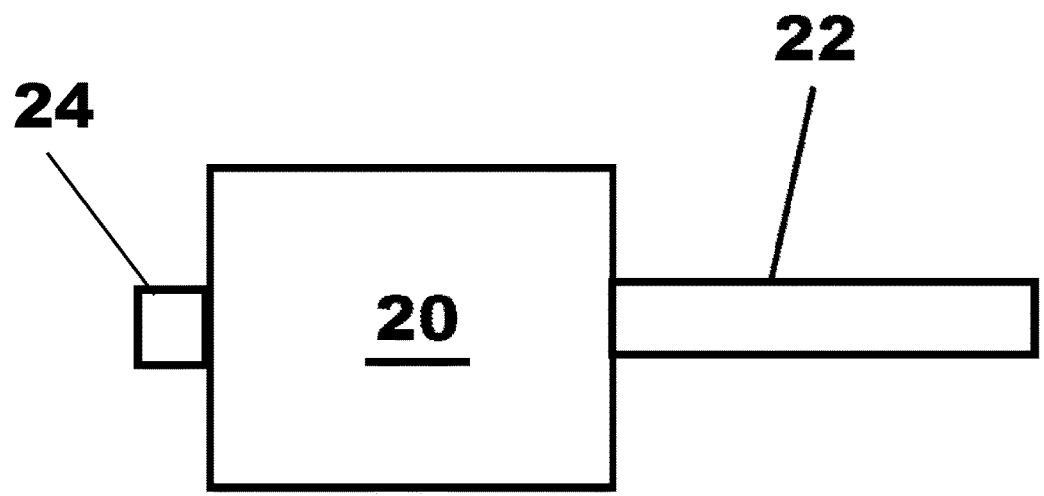

FIG. 1: Schematic picture of the emergency supply valve.
FIG. 2: Schematic picture of the emergency valve wherein the needle is in the forward position.
FIG. 3: Schematic picture of an implantable pump with a self-sealing service port and an output line for use with the emergency supply valve.

DETAILED DESCRIPTION OF THE INVENTION

The present invention provides an emergency supply valve to support the in situ administration of a drug solution from a regular drug conduit to a subject in need thereof, comprising
  a. an infusion needle (1) connected to a movable piston (2),
  b. a pressure sensitive system that pushes said piston (2) into a forward position due to an increased drug overpressure of the drug solution which is accumulated as it is unable to pass the regular drug supply conduit (5),
  c. a self-sealing membrane (3) in front of the needle tip, and
  d. a connecting unit (4) that is connected to the infusion needle and the moveable piston and provides connection to the regular drug conduit (5) for drug flow when the needle is in a forward position.

According to a further embodiment, the present invention provides an emergency supply valve to support the in situ administration of a drug solution from a regular drug conduit to a subject in need thereof, comprising
  a. an infusion needle (1) connected to a movable piston (2),
  b. a pressure sensitive system that allows said piston (2) to move into a forward position due to an increased drug overpressure of the drug solution which is accumulated as it is unable to pass the regular drug supply conduit (5), specifically the piston overcomes the resistance of the pressure sensitive system in the presence of an increased drug overpressure.
  c. self-sealing membrane (3) in front of the needle tip, and
  d. a connecting unit (4) that is connected to the infusion needle and the moveable piston and provides connection to the regular drug conduit (5) for drug flow when the needle is in a forward position.

When moving the needle into the forward position, the self-sealing membrane is punctured and the drug fluid can be administered through the needle.

In a specific embodiment, the emergency supply valve can be incorporated in a housing (18) accommodating all elements of the valve or it can be integrated directly into the catheter line. In case the supply valve is in the housing (18), said housing (18) may be directly connected or fixed to the drug supply system thus avoiding possible kinking or blocking of any connecting elements.

The term "housing" according to the invention can mean any case, sheath, shell or cover of any shape or size which can be made of any material known to be applicable for implantation. Specifically, the housing may be of cylindrical shape. Said housing may contain one or more openings for connecting with the drug supply line.

According to an embodiment of the invention, the housing contains
  a. an infusion needle (1) connected to a movable piston (2),
  b. a retaining spring (8) that allows the piston to move into a forward position at an increased overpressure of the drug solution, specifically the retaining spring prevents the piston from moving into the forward position in the presence of normal overpressure of the drug solution,
  c. a self-sealing membrane (3) placed in front of the needle tip,
  d. a connecting unit (4) attached to the needle, wherein the connecting unit is sealed off the regular drug conduit when the needle is in the retracted state and is connected to the regular drug conduit when the needle is in the forward state penetrating the membrane and optionally
  e. two sealing rings (6 and 7), at least one protecting the retaining spring and
  f. a supporting line interconnecting the chamber containing the needle (9 and 10) and the chamber containing the retention spring (11).

According to a further specific embodiment of the invention, the housing contains
  a. an opening for the drug supply line,
  b. a chamber with an infusion needle (1) connected to a movable piston (2),
  c. a chamber containing the retaining spring (8) the that allows the piston to move into a forward position at an increased overpressure of the drug solution, specifically the retaining spring prevents the piston from moving into the forward position in the presence of normal overpressure of the drug solution,
  d. a self-sealing membrane (3) placed in front of the needle tip,
  e. a connecting unit (4) attached to the needle, wherein the connecting unit is sealed off the regular drug conduit when the needle is in the retracted state and is connected to the regular drug conduit when the needle is in the forward state penetrating the membrane and optionally
  f. two sealing rings (6,7), at least one protecting the retaining spring and optionally
  g. a supporting line interconnecting the chamber containing the needle (10) and the chamber containing the retention spring (11).

As an alternative, a device comprising a body, an infusion needle which is connected to a movable piston, a self-sealing membrane in front of the needle tip, and a connecting unit attached to the needle and connecting the infusion needle to the regular drug conduit to allow free flow of the drug fluid from the output line when the needle is in the forward position and comprising a pressure sensitive mechanism for retracting the piston from the forward position is provided by the invention.

The connecting unit can be for example a tube, a hose or a pipe. Specifically the unit is rigid or semi-rigid, specifically it is made of a material known for infusion devices, specifically, it may be made of plastic or any polymer suitable for medical systems.

The regular drug line is a medication conduit that directly supplies the drug into the venous system, for example into a central vein.

In a specific embodiment the regular drug conduit (15) is connected to a supporting line which enables drug flow between the regular drug conduit (15) and/or the chamber containing the pressure sensitive system and/or the chamber containing the needle when being in the resting position and the connecting unit when the needle is in the forward position.

Said supporting line specifically can comprise branched tubes connecting the sectors of the emergency supply device with the regular drug conduit.

More specifically, the supporting line (9) connects the chamber with the needle and the chamber containing the retention spring.

In a further embodiment, a pressure sensitive mechanism retracts the piston from the forward position and fixes it in the resting position when the increased over pressure of the drug solution is normalized.

The pressure sensitive system (14) comprises a retaining or return spring (8) connected to the movable piston which assists to move the piston with the infusion needle into its resting position. Preferably, the retaining spring is made of non-magnetizable material which avoids any issues upon using magnetic resonance as diagnosing means for the implant carrying subject. More specifically, the spring is composed of non-ferrous metal, more specifically it is made of titanium.

The emergency supply valve may comprise one, specifically two sealing rings, optionally more than two sealing rings, also termed O rings (6, 7). Specifically, the second sealing ring (7) protects and seals or closes the space containing the retaining spring (8). Optionally, more than two, specifically 3, 4, 5 or more than 5 sealing rings can be present in the supply valve device.

The sealing rings are preferably placed between the opening for the connecting unit (16) which allows drug flow when the needle is in the forward position and the pressure sensitive system.

The term "overpressure" according to the invention means a drug conduit pressure greater than body pressure needed for continuous drug supply. Specifically, said overpressure threshold of ≤200 kPA, specifically up to an overpressure threshold of ≤150 kPA, specifically up to an overpressure threshold of ≤100 kPA.

The term "increased overpressure" means a pressure of >200 kPA, specifically of >150 kPA, specifically of >100 kPA, with the proviso that the increasing pressure does not exceed 250 kPA.

Upon increased overpressure in the regular drug delivery system, specifically in the output line, the pressure within the emergency supply system increases and the piston together with the infusion needle is moved into a forward position. Thereby, the connecting unit is moved forward from the resting position between the sealing rings towards an auxiliary opening of the regular drug conduit and thus the drug can be supplied via the infusion needle which punctures the sealing membrane. By supplying the drug via the alternative route, the pressure may decrease, the piston and the needle are retracted towards the resting position, and the alternative supply is stopped as the connecting unit is closed by the first sealing ring. If the regular supply is continuously blocked, the pressure again increases and the process of forwarding the infusion needle is repeated. This process may be repeated until the blockage of the regular supply system is cleared.

Thus, if overpressure in the regular drug delivery system increases, the drug solution is delivered through the drug supply conduit (5), against the resistance of the retention spring, into the chamber and moves the piston and the needle into the forward position. The gas or liquid in front of the piston escapes or is pressed out via the supporitng line (9) into the chamber containing the retention spring. When the needle penetrates the septum, lines (5) and (4) are connected and are communicating and the drug solution is administered into the tissue.

Restoring of the regular supply pathway via the central venous catheter will also restore normal pressure of the drug supply and thereby cause retraction of the piston which will bring the infusion needle back into its resting position.

The top of the emergency supply valve is defined as the part where the self-sealing membrane is placed, the bottom of said valve is defined as the part where the pressure sensitive system (14) is located.

The term "forward" according to the invention means that the infusion needle is moved towards the self-sealing membrane which is positioned in front of the infusion needle tip. The term "forward position" or "forward state" according to the invention means the position of the infusion needle wherein the tip of the infusion needle has protruded the self-sealing membrane and, if a connective tissue was developed by the subjects organism, the connective tissue capsule.

The term "resting position" or "basic position" or "retracted position" means that the infusion needle is retracted or moved back to its resting position and does not protrude the self-sealing membrane. Thus the needle is at a position wherein no connection to the drug supply via the connecting unit exists.

According to an embodiment of the invention, the infusion needle is a hollow needle with a tube-like body with a tip end, specifically it has a beveled tip (13). Therefore, the needle will not cut out any material of the membrane but will simply divide it during penetration. Thus, when the needle penetrates the membrane, such as the self-sealing penetration membrane, there will be no material entering and blocking the drug delivery passageway.

After the implantation, devices are normally encapsulated by connective tissue sheaths which hold the implants firmly at their positions. These connective tissue sheaths are physiologically meant to isolate foreign bodies and would, hence, obstruct any simple bypass mechanism intended to reroute inefficient venous drug delivery into the subcutaneous space. An efficient bypass must therefore be able to reliably overcome this natural barrier. The infusion needle used in the emergency supply valve according to the invention shall have a length sufficient to penetrate the membrane and pass through the connective tissue barriers. Preferably, said infusion needle has about 3 to 5 mm excess length, however the needle may also be longer than 5 mm, specifically about 5.5, 6, 6.5 or 7 mm.

The term "excess length" means the length of the needle part that protrudes the sealing membrane.

According to an embodiment of the invention, the self-sealing membrane used in the emergency supply valve and optionally also used in the injection port for refilling the drug from outside the human body into the drug reservoir is made from polymeric material. Specifically, the self-sealing material may be made from a polymeric material which preferably comprises silicon or poylurethane. Other biocompatible polymeric materials may be employed as well.

The self-sealing material may also be a composite material. Exemplarily, such composite material may comprise at least one outer shape-giving layer and a self-sealing soft material contained within the outer layer. Thus, the outer layer forms a shell for the soft material and may be made from a biocompatible polymer, such as one of those polymers mentioned above, and the self-sealing soft material may be a gel.

According to a further embodiment, the needle stays in resting position up to an overpressure threshold of ≤200 kPA, specifically up to an overpressure threshold of ≤150 kPA, specifically up to an overpressure threshold of ≤100 kPA. According to a further embodiment, the needle is forwarded with increasing overpressure of >200 kPA, specifically with increasing overpressure of >150 kPA, specifically with increasing overpressure of >100 kPA, wherein the increasing pressure is not more than 250 kPA.

Specifically, the pressure sensitive system or mechanism which is a retraction spring and which is connected to the piston is designed to keep the needle in the resting or forward position at the respective overpressures. The retaining spring would, in case the pressure decreased following resolving of the occlusion of the regular drug delivery line, withdraw the piston and, thereby, reset the hollow needle into its basic resting position, specifically behind the self-sealing membrane. The emergency valve would so maintain its functionality and render a surgical exchange intervention unnecessary.

The invention also provides a setup or device or implantable system comprising a pump and a supply unit, wherein the supply unit consists of an output line (22), the inventive emergency supply valve, wherein the output line constantly supplies the drug intravenously to a subject and the emergency supply valve administers said drug in case when the intravenous route is blocked by an alternative administration route, specifically by a subcutaneous route, and wherein said emergency supply valve is specifically placed between the implantable pressure pump, specifically a micropump, and a central venous access point.

The term "output line" means a catheter system or catheter line made of silicone or polyurethane which is tunneled subcutaneously from the pump to a central vein access such as the subclavian vein.

The term "subject" includes humans and animals, specifically mammalians. Subjects can be any individual or patient in need of constant drug supply.

The pump may be any implantable pump, specifically it contains a sealed reservoir containing the drug solution.

Pump and emergency valve are preferably joined together within close vicinity by means of a catheter line and may be specifically fixed to the abdominal muscular fascia. The emergency valve thereby guards the proper discharge of the pumps reservoir into the central venous catheter line by providing an alternative subcutaneous drug delivery option, in case of malfunction of the regular central venous supply route.

The pump does have a fill port including a septum made of a self-sealing material for injecting the drug from outside of the body into the pump reservoir. Said reservoir may be a titanium bellows. The bellows provides a flexible boundary between the medication and a gas pressure chamber. Filling of the pump pressurizes gas that is stored below the reservoir. Drug delivery thereafter is provided by constant gas pressure on the pump reservoir. Any pump which can beimplanted can be used for the system of the invention. Specifically, the preceding pump contains a self-sealing service port (24) which allows rinsing of the catheter line.

Implantable micropumps usually operate on a carburetted hydrogen gas which is compressed by a bellows when infusion solution is instilled into the device. Once charged these pumps are able to push medication solution at a pressure of up to 100 kPa, specifically up to 200 kPa into the central venous catheter. The central venous pressure per se numbers about 0.2-0.5 kPa. That means that the pressure difference will under regular circumstance always keep the central venous line open and functional. Catheter kinking could under exceptional circumstance lead to an occlusion of the line between the active emergency supply valve and the central venous access point and thereby lead to increased infusion pressure. As a consequence the increased pressure in the emergency supply valve would forward the piston, make the hollow needle pass the silicon membrane plus the connective tissue capsule, thereby generating a reliable bypass for alternative drug supply via the subcutaneous route. Since most of the patients would experience local pain and irritation at the subcutaneous injection site, the impairment of the regular intravenous route would become evident within several minutes to hours. The stretched status of the retaining spring will under x-ray control finally reveal whether the emergency valve has been activated or not. The device mechanism may not need or does not have any valves or mechanical parts in the direct pump to venous access point catheter. This allows uncomplicated flushing of the catheter via a service access point of the pump. Successful catheter reopening procedures via a pump service port would result in re-establishment of the regular intravenous infusion pathway. Re-established patency of a previously occluded venous access line will, due to the restored basic pressure situation, lead to a mechanical auto resetting of the valve which may spare the patient a burdening surgical device revision.

The emergency supply valve according to the invention or a setup containing the valve may specifically comprise a housing (18) which allows suturing of the implant into surrounding tissue at several points to immobilize said implant at the implantation site.

The housing may be manufactured from any material that is biocompatible and hermetically sealed such as titanium, tantalum, stainless steel, plastic, ceramic and the like.

Drug delivery by the implantable pump (20) will, via the regular central venous route, not be noticeable by the patient. Activation of the emergency supply valve will cause alternative subcutaneous deposition of the drug, which usually goes along with local irritation and pain at the injection site. In this case, this otherwise harmless side effect would alert the patient to seek medical aid. The drug must be stable in the implanted drug reservoir at least for the time until the next pump refill. This would usually be a period of at least four weeks.

Specifically, the drug may be selected from the group of prostaglandin or prostanoid analogs, for example, but not limited to treprostinil, iloprost, cicaprost, beraprost or derivatives or pharmaceutically acceptable salts thereof, or from the group of PDE5 inhibitors like for example but not limited to sildenafil and tadalafil, from the group of endothelin receptor antagonists, for example but not limited to ambrisentan, bosentan, Actelion-1 and sitaxentan or from soluble guanylate cyclases.

Parenteral prostanoid analogues which can be administered intravenously and subcutaneously are preferred drugs for use according to the invention.

According to a specific embodiment, the emergency supply valve can be used in an implantable system for the intravenous treatment of pulmonary arterial hypertension. The present invention provides also a method for administering a drug to a subject in need thereof by using the emergency supply valve in a setting as described above. Specifically, the system provides a method for setting an alarm wherein a drug is administered that causes mild to moderate local pain or irritation upon subcutaneous administration by the emergency supply valve and alerts the subject to seek medical aid.

The invention furthermore comprises the following items:
1. Emergency supply valve to support the in situ administration of a drug solution from a regular drug conduit to a subject in need thereof, comprising
    a) an infusion needle connected to a movable piston,
    b) a pressure sensitive system that pushes the piston into a forward position at an increased overpressure of the drug solution that is unable to pass the regular drug supply line,
    c) a self-sealing membrane placed in front of the needle tip,
    d) a connecting unit attached to the needle, wherein the connecting unit is sealed off the regular drug conduit when the needle is in the retracted state and is connected to the regular drug conduit when the needle is in the forward state penetrating the membrane.
2. Emergency supply valve to support the in situ administration of a drug solution from a regular drug conduit to a subject in need thereof, comprising
    a) an infusion needle (1) connected to a movable piston (2),
    b) a pressure sensitive system that allows said piston (2) to move into a forward position due to an increased drug overpressure of the drug solution which is accumulated as it is unable to pass the regular drug supply conduit (5), specifically the piston overcomes the resistance of the pressure sensitive system in the presence of an increased drug overpressure.
    c) self-sealing membrane (3) in front of the needle tip, and
    d) a connecting unit (4) that is connected to the infusion needle and the moveable piston and provides connection to the regular drug conduit (5) for drug flow when the needle is in a forward position.
3. The emergency supply valve of item 1 or 2, further comprising a supporting line connecting the pressure sensitive system and the chamber containing the needle.
4. The emergency supply valve of item 1 or 2, further comprising a supporting line connecting the regular drug supply conduit with a) the pressure sensitive system, b) the chamber containing the needle and c) the connecting unit.
5. The emergency supply valve of items 1 to 4, wherein said piston comprises surfaces upon which the pressure of the fluid in the regular drug supply line acts.
6. The emergency supply valve according to any one of items 1 to 5, wherein the pressure sensitive mechanism retracts the piston from the forward position.
7. The emergency supply valve according to any one of items 1 to 6, wherein the pressure sensitive system is a retaining spring connected to the movable piston.
8. The emergency supply valve according to item 1 to 7 wherein the drug is administered subcutaneously.
9. The emergency supply valve according to items 1 to 8, wherein the needle is a hollow needle with a beveled tip.
10. The emergency supply valve according to any one of items 1 to 9, wherein the infusion needle has a length sufficient to penetrate the membrane and pass through the scar tissue capsule around the implant, preferably said needle has 3 to 5 mm excess length.
11. The emergency supply valve according to any one of claims 1 to 10, comprising one or more sealing rings, wherein said sealing rings are placed behind the opening for the connecting unit.
12. The emergency supply valve according to any one of items 1 to 11, wherein the self-sealing membrane is made from polymer material.
13. The emergency supply valve according to any one of items 1 to 12, wherein the polymer material comprises at least one polymer selected from the group of materials comprising silicon and polyurethane.
14. The emergency supply valve according to any one of items 1 to 13, wherein the metal parts such as retaining spring and needle are made of non-magnetizable material.
15. The emergency supply valve according to any one of items 1 to 14, wherein the increased pressure in the drug supply line is due to blockage of the intravenous catheter coupled to the emergency supply valve.
16. The emergency supply valve according to any one of items 1 to 15, wherein the needle is in resting position up to an overpressure threshold of ≤200 kPA, specifically up to an overpressure threshold of ≤150 kPA, specifically up to an overpressure threshold of ≤100 kPA.
17. The emergency supply valve according to any one of items 1 to 16, wherein the needle is forwarded with increasing overpressure of >200 kPA, specifically with an overpressure of >150 kPA, specifically with an overpressure of >100 kPA.
18. The emergency supply valve according to any one of items 1 to 17, wherein the connecting unit gains access to the regular infusion conduit if the needle is in the forward position.
19. A setup comprising an implantable pressure pump and a supply unit, wherein the supply unit comprises an output line the emergency supply valve according to any one of items 1 to 18, wherein the output line constantly supplies the drug intravenously to a subject and the emergency supply valve optionally administers said drug by an alternative administration mode and wherein said emergency supply valve is placed between the pump and a central venous access point.
20. The emergency supply valve according to any one of items 1 to 18 or a setup according to claim 19, wherein said valve is covered by a housing allowing suturing of the housing into surrounding tissue to immobilize said housing at the implantation site.
21. The setup according to items 19 or 20, wherein a preceding pump further comprises a power source and a refillable drug containing reservoir.
22. The setup according to any one of items 19 to 21, wherein the preceding pump contains a self-sealing service port which allows rinsing of the catheter line.
23. The setup according to any one of items 19 to 22, wherein restoring of the regular supply pathway via the central venous catheter retracts the piston and brings the infusion needle back into its resting position.
24. A method for administering a drug to a subject in need thereof by using the emergency supply valve in a setting to any one of items 1 to 23.
25. The method according to item 24 wherein a drug is administered that causes mild to moderate local pain or irritation upon subcutaneous administration by the emergency supply valve and alerts the subject to seek medical aid.

The invention claimed is:
1. An emergency supply valve in a housing to support in situ administration of a drug solution from a regular drug conduit to a subject in need thereof, comprising: a. an infusion needle with a beveled needle tip in a needle chamber connected to a movable piston, b. a self-sealing membrane placed in front of the beveled needle tip, c. a drug supply conduit in communication with the regular drug conduit and the piston, d. a retention spring chamber containing a retaining spring, wherein the retaining spring is connected to the piston, and wherein the piston and the needle can be pushed from a retracted position in which the needle tip does not protrude through the membrane to a forward position in which the needle tip protrudes through the membrane against resistance from the retention spring by increased pressure of drug solution from the drug supply conduit, and d e. a connecting unit conduit attached to the needle and the piston, wherein the connecting conduit is placed into communication with the drug supply conduit by movement of the piston and the needle into the forward position and is sealed off from the drug supply conduit when the needle is in the retracted position.

2. The emergency supply valve of claim 1, wherein said piston comprises surfaces upon which a pressure of the drug solution from the regular drug conduit acts.

3. The emergency supply of claim 1, wherein the retaining spring retracts the piston from the forward position in response to decreased pressure of drug solution from the drug supply conduit.

4. The emergency supply of claim 1, wherein the drug solution is administered subcutaneously.

5. The emergency supply of claim 1, wherein the needle is a hollow needle with the beveled tip.

6. The emergency supply of claim 1, wherein the needle has a length sufficient to penetrate the self-sealing membrane when the piston is pushed in the forward position and pass through a scar tissue capsule covering an outer surface of the self-sealing membrane.

7. The emergency supply of claim 1, wherein the needle has a length of 3 to 5 mm past the self-sealing membrane when in the forward position.

8. The emergency supply valve of claim 1, comprising one or more sealing rings, wherein said sealing rings seal the retention spring chamber containing the retaining spring.

9. The emergency supply valve of claim 1, wherein the self-sealing membrane is made from a polymeric material.

10. The emergency supply valve of claim 1, wherein the needle is in the retracted position up to an overpressure threshold of <200 kPA.

11. A system comprising an implantable pressure pump and a supply unit, wherein the supply unit comprises:
    a) an output line; and
    b) the emergency supply valve of claim 1, wherein said emergency supply valve is placed distally with respect to the pump.

12. The system of claim 11, wherein the housing allows suturing of the housing into surrounding tissue to immobilize said housing at an implantation site.

13. The system of claim 11, wherein the pump contains a self-sealing service port which allows rinsing of the output line.

14. The system of claim 11, wherein restoring flow through the regular drug conduit retracts the piston and brings the needle back into its retracted position.

15. A method for administering a drug solution to a subject in need thereof using the emergency supply valve of claim 1, comprising the steps of:
    moving the needle of the emergency supply valve into the forward position;
    puncturing the self-sealing membrane of the emergency supply valve; and
    administering a fluid comprising the drug solution to the subject through the needle of the emergency supply valve.

16. The method according to claim 15 wherein the drug solution causes local pain or irritation upon subcutaneous administration by the emergency supply valve.

17. The emergency supply valve of claim 9, wherein the polymeric material is silicon or polyurethane.

18. The emergency supply valve of claim 10, wherein the needle is in the retracted position up to the overpressure threshold of <100 kPA.

* * * * *